(12) United States Patent
Hwang et al.

(10) Patent No.: US 8,722,617 B2
(45) Date of Patent: May 13, 2014

(54) MUSSEL ADHESIVE PROTEIN DERIVED VECTORS FOR GENE DELIVERY

(75) Inventors: Dong Soo Hwang, Pohang (KR); Hyung-Joon Cha, Pohang (KR)

(73) Assignees: Postech Academy-Industry Foundation, Pohang (KR); Posco, Pohang-Shi (KR)

( * ) Notice: Subject to any disclaimer, the term of this patent is extended or adjusted under 35 U.S.C. 154(b) by 893 days.

(21) Appl. No.: 12/344,773

(22) Filed: Dec. 29, 2008

(65) Prior Publication Data

US 2009/0186413 A1 Jul. 23, 2009

Related U.S. Application Data

(60) Provisional application No. 61/017,857, filed on Dec. 31, 2007.

(51) Int. Cl.
*A61K 38/00* (2006.01)
*A61K 48/00* (2006.01)

(52) U.S. Cl.
USPC .......................... 514/1.2; 514/44 R; 514/44 A

(58) Field of Classification Search
None
See application file for complete search history.

(56) References Cited

FOREIGN PATENT DOCUMENTS

| WO | 2005/092920 | 10/2005 |
|---|---|---|
| WO | 2006/107183 | 10/2006 |
| WO | 2008/150101 | 12/2008 |

OTHER PUBLICATIONS

Knight, et al. (1999) European Journal of Biochemistry, 259: 762-69.*
Faure, et al. (2009) Materials Science and Engineering C, 29: 1252-57.*
http://www.ncbi.nlm.nih.gov/protein/CAL85229.1.*
Jung et al., *Carassius auratus*—Originated Recombinant Histone H1 C-Terminal Peptide as Gene Delivery Material, Biotechnol. Prog. vol. 24. pp. 17-22, 2008.
Cha et al., Development of bioadhesives from marine mussels, Biotechnology Journal, 3(5), 631-638 2008.
Hwang et al., Practical recombinant hybrid mussel bioadhesive fp-151, Biomaterials vol. 28, pp. 3560-3568, 2007.
Gim et al., Production of Fusion Mussel Adhesive fp-353 in *Escherichia coli*, Biotechnol. Prog. vol. 24, pp. 1272-1277, 2008.

* cited by examiner

*Primary Examiner* — Robert M Kelly
(74) *Attorney, Agent, or Firm* — Lexyoume IP Meister, PLLC

(57) ABSTRACT

The present invention is related to a composition and a method for delivering a nucleic acid into a cell. The invention also provides a biocompatible and biodegradable gene delivery composition and methods of use and making thereof.

10 Claims, 6 Drawing Sheets

MUSSEL ADHESIVE PROTEIN DERIVED VECTORS FOR GENE DELIVERY

CROSS REFERENCE TO RELATED APPLICATION

The present application claims priority to and the benefit of U.S. Ser. No. 61/017,857, filed Dec. 31, 2007 with United States Patent and Trademark Office which is hereby incorporated by reference for all purposes as if fully set forth herein.

FIELD OF THE INVENTION

The present invention relates to a new use of a peptide derived from mussel adhesive protein. More specifically, the present invention provides a composition and a method for delivering a nucleic acid sequence into eukaryotic cells comprising contacting the cells with a mixture of the nucleic acid sequence and a gene-delivering peptide comprising a peptide derived from a mussel adhesive protein.

BACKGROUND

This invention relates to gene delivery and gene therapy. More particularly, the invention relates to compositions and methods for use, and making thereof, for delivering nucleic acids as genomic DNA, RNA, or any nucleic acid analogue, including but not limited to aptamer, for life science applications, or other non-soluble bioactive molecules such as protein, peptides or small non-soluble drugs.

There are a number of techniques for the introduction of genes into cells. One common method involves viruses that have foreign genes (e.g., transgenes) incorporated within the viral DNA. However, the viral genes are also delivered with the desired gene and this can lead to undesirable results.

To address some problems encountered in viral vectors, non-viral gene delivery systems such as cationic liposomes or synthetic gene carriers have been widely sought as alternatives and investigated intensively.

The carrier molecules bind and condense DNA into small particles which facilitate DNA entry into cells through endocytosis or pinocytosis. In addition, the carrier molecules act as scaffolding to which ligands may be attached in order to achieve site specific targeting of DNA.

The most commonly used DNA condensing agent for the development of non-viral gene delivery systems is polylysine in the size range of dp 90-450. Its amino groups have been derivatized with transferrin, glycoconjugates, folate, lectins, antibodies or other proteins to provide specificity in cell recognition, without compromising its binding affinity for DNA. However, the high molecular weight and polydispersity of polylysine also contribute to a lack of chemical control in coupling macromolecular ligands which leads to heterogeneity in polylysine-based carrier molecules. This can complicate the formulation of DNA carrier complexes and limits the ability to systematically optimize carrier design to achieve maximal efficiency.

In general, polycationinic polymers are known to be toxic and the PLL backbone is barely degraded under physiological conditions. It will remain in cells and tissue which can cause undesirably high toxicity.

Biodegradable polymers, such as polylactic/glycolic acid (negatively charged), and polylactide/glycolide (neutral) have been used as gene carriers in the form of non-soluble particulates.

Cationic liposomes are commercialized non-viral carriers due to their non-immunogenicity and simplicity of large-scale production. However, their efficiencies can be relatively low due to inactivation by serum or blood components and loose condensation of DNA associated with decreased uptake into cells.

To overcome the problems of liposomes, polymer systems or cationic proteins have been introduced. The cationic protein-based gene delivery system has several advantages, including ease of use in serum- and/or antibiotic-containing medium, the ability to target nucleic acids to specific cell types, no limit on the size or type of target nucleic acid, possibility of modular attachment of targeting ligands, and the potential for cost-effective, large-scale manufacture.

A number of histone proteins have been widely analyzed as potential gene delivery materials. Histones display similar or higher transfection efficiency in mammalian cells, compared to the widely used transfection agent, Lipofectamine (Jung et al., Biotechnol. Prog. vol 24. pp 17-22, 2008). Histones are basic proteins that contain several lysines and arginines. These positively charged amino acids facilitate electrostatic interactions with the negatively charged phosphate backbone of DNA. However, application of eukaryotic histones for gene delivery is limited by low recombinant expression levels and infection risks.

The invention aims at eliminating some of the major disadvantages and limitations of the known techniques described above. Firstly, it aims at providing a gene carrier that is non toxic, biodegradable, and/or biocompatible. Secondly, it provides a gene carrier composition that is efficient and viable under in vivo conditions such as serum condition.

SUMMARY OF THE INVENTION

It is an object of the present invention to provide a composition and a method for delivering a nucleic acid into a cell.

It is also an object of the present invention to provide a biocompatible and biodegradable gene delivery composition and methods of use and making thereof.

It is yet another object of the invention to provide a non-toxic, soluble, biodegradable, non-viral composition and a method of use thereof, for delivering exogenous nucleic acids into a targeted cell.

These objects can be achieved by providing a cationic protein, mussel adhesive protein.

In an embodiment of the present invention, it is to provide a method for delivering a nucleic acid sequence into eukaryotic cells comprising contacting the cells with a mixture of the nucleic acid sequence and a gene-delivering peptide comprising a peptide derived from a mussel adhesive protein.

In another embodiment, it is to provide a method of delivering a selected nucleic acid into a selected cell comprises the steps of:

(a) mixing an effective amount of the selected nucleic acid with an effective amount of mussel adhesive protein to form a complex;

(b) contacting the selected cell with the complex under the conditions that the nucleic acid and the gene-delivering peptide are delivered across the cell membrane.

BRIEF DESCRIPTION OF THE DRAWINGS

These and other features and advantages of the present invention are evident from the following embodiments when read in conjunction with the accompanying drawings in which.

DETAILED DESCRIPTION

Figure 1:
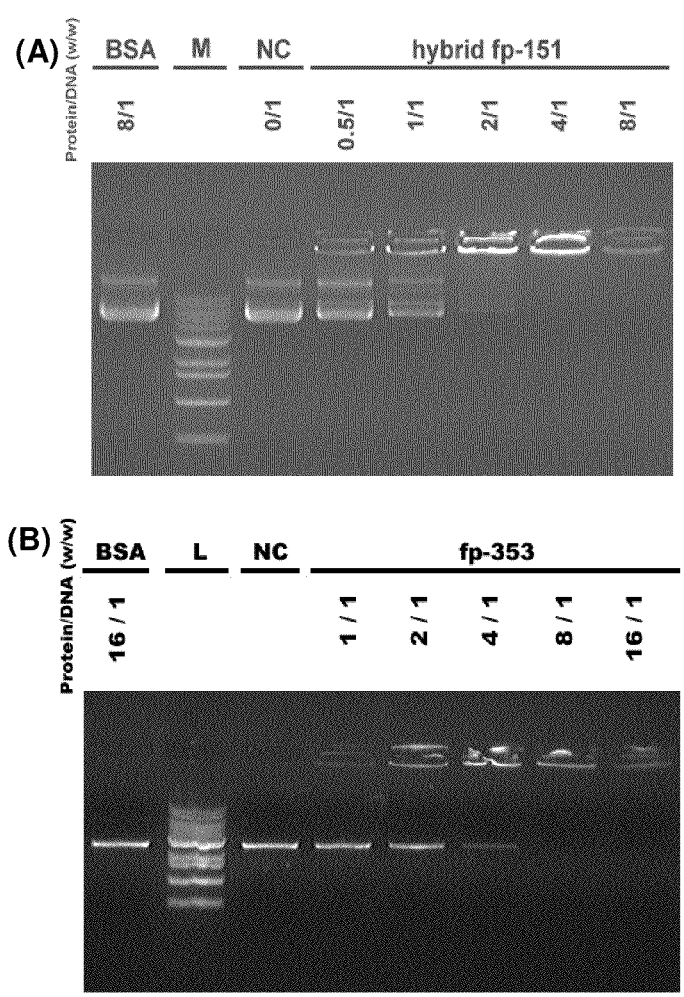
FIG. 1 shows DNA retardation assay to determine the DNA-binding activity of (A) hybrid fp-151 and (B) hybrid fp-353.

The present invention provides mussel protein based gene carrier composition comprising a recombinant mussel adhesive protein, wherein the recombinant mussel protein is genetically engineered with numerous affinity peptides for specificity.

Before the present mussel protein based gene carrier composition and methods of making and using thereof are disclosed and described, it is to be understood that this invention is not limited to the particular configurations, process steps, and materials disclosed herein as such configurations, process steps, and materials may vary somewhat. It is also to be understood that the terminology employed herein is used for the purpose of describing particular embodiments only and is not intended to be limiting since the scope of the present invention will be limited only by the appended claims and equivalents thereof.

It must be noted that, as used in this specification and the appended claims, the singular forms "a," "an," and "the" include plural referents unless the context clearly dictates otherwise.

The term "nucleic acid" as used here shall mean the polymeric form of nucleotides of any length, including but not limited to, DNA, RNA and hybrids thereof. The nucleic acid bases that form nucleic acid molecules can be the bases A, C, G, T and U, as well as derivatives thereof. The DNA can either be cDNA or genomic DNA. The term further comprises the non-modified form as well as scientifically known modifications, e.g., methylation, capping, base substitution with natural or synthetic analogues, internucleotide modifications with uncharged compounds (e.g., methyl phosphate, phosphoamidate, carbamate, phosphotriester and the like) or with charged compounds (e.g., phosphorothioate, phosphorodithioate and the like) or with binding components such as proteins and peptides (e.g., nucleases, toxins, antibodies, poly-L-lysine, and the like). The term also comprises forms with intercalating substances (e.g., acridin, psoralen, and the like), chelators (e.g., with metals, radioactive metals or oxidizing metals and the like), with alkylating agents and finally with modified bonds (e.g., alpha anomeric nucleic acids, and the like).

In an embodiment of the present invention, the gene-delivering peptide comprising a peptide derived from a mussel adhesive protein (MAP) is used for delivering a nucleic acid into a target cell. The peptide derived from a mussel adhesive protein is a protein, a fragment, and a fusion peptide of at least one selected from mussel foot protein (FP)-1, FP-2, FP-3, FP-4, FP-5, and FP-6. The term "mussel adhesive protein" as used here shall mean a protein with adhesiveness derived from mussel, for examples, the peptide derived from a mussel adhesive protein is a fusion protein comprising a first domain which is a FP-5 or a fragment thereof and a second domain which is at least one selected from the group consisting of FP-1, FP-2, FP-3, FP-4, and FP-6, and the second domain is linked to C-terminus, N-terminus or C- and N-terminus of the FP-5. The FP-5 comprises an amino acid sequence of SEQ ID NO:1. The example of FP-1 comprises six repeats of FP-1 decapeptide which is an amino acid sequence of SEQ ID NO:2. An example of FP-3A comprises an amino acid sequence of SEQ ID NO:3. The examples of the fusion peptide derived from the mussel adhesive proteins are FP-151 including an amino acid sequence of SEQ ID NO:3 and FP-353 including an amino acid sequence of SEQ ID NO:5.

The gene-delivering peptide further comprises a purification tag, for example hexa histidine tag (6His) for simple purification, or a nuclear localization signal peptides (NLS) and a protein transduction domain (PTD) for enhancement of transfection efficiency. The examples of nuclear localization signal peptides (NLS) are amino acid sequences of SEQ ID NO: 6 to SEQ ID NO:8. The examples of protein transduction domain (PTD) are amino acid sequences of SEQ ID Nos: 9 to 12. The examples of purification tag are amino acid sequences of SEQ ID Nos.: 13 to 17.

| classification | Amino acid sequence | SED ID NO |
|---|---|---|
| NLS | PKKKRKVEDPYC | 6 |
| NLS | CGGPKKKRKVG | 7 |
| NLS | PPKKKRKV | 8 |
| PTD | RKKKRRQRRR | 9 |
| PTD | DAATATRGRSAASRPTERPRAPARSASRPRRPVE | 10 |
| PTD | RQIKIWFQNRRMKWKK | 11 |
| PTD | AGYLLGKINLKALAALAKKIL | 12 |
| Purification tag | HHHHHH | 13 |
| Purification tag | DYKDDDDK | 14 |
| Purification tag | YPYDVP | 15 |
| Purification tag | ILKKATAYIL | 16 |
| Purification tag | EQKLISEEDL | 17 |

The gene-delivering peptide comprising a peptide derived from the mussel adhesive protein and hexa-histidine (6His) can be easily synthesized with the well engineered E. coli bacteria to produce a variant of the mussel adhesive proteins in an efficient way (see Cha et al. Biotechnology Journal, 3(5), 631-638 2008; WO 2005/092920, WO 2006/107183, and WO2008/150101 which are hereby incorporated by reference for all purposes as if fully set forth herein), and the proteins are commercially available under Trademarks MAP-Trix™ marketed by Kollodis BioSciences, Inc. This method provides a recombinant expression system for large scale production of mussel adhesive protein with amazingly low cost and adhesiveness.

In one embodiment, hybrid MAP (fp-151 or fp-353) fused with the hexa-histidine affinity ligand was prepared with ~95% purity using IMAC to eliminate E. coli components with possible negative effects on mammalian cell culture. We investigated the DNA binding ability of purified hybrid fp-151 and fp-353 using a gel retardation assay. The electrophoretic mobility of DNA on a 1% agarose gel was retarded in the presence of hybrid MAP, in proportion to the amount of protein. Moreover, the hybrid fp-151/plasmid DNA complex displayed completely retarded migration on the agarose gel at a hybrid fp-151:DNA ratio of 4:1 (wt/wt). Thus, the minimum ratio for complete binding of hybrid fp-151 with plasmid DNA was estimated as ~4:1 (wt/wt). In the case of fp-353, the minimum ratio for complete binding with plasmid DNA was estimated as ~8:1 (wt/wt)

To maximize transient transfection efficiency, the mixing ratio (wt/wt) of hybrid MAP to plasmid DNA harboring lacZ gene as the reporter may be needed. The concentration of calcium ion used for optimal binding ratio between hybrid MAP and DNA in the medium was 0 to 20 mM, in considering the transfection efficiency and harmful effect on the cell In one embodiment, the mixing ratio by weight of hybrid fp-151 to DNA is 1:1 to 100:1, in considering the transfection efficiency, suitable DNA binding and harmful effect on the cell.

The following examples are provided to demonstrate preferred embodiments of the present invention and the invention is not to be limited in scope by the specific embodiments described herein, which are intended for the purposes of exemplification only. Functionally equivalent products, compositions and methods are clearly within the scope of the invention, as described herein.

Example 1

Expression of Recombinant Mussel Adhesive Protein fp-151 and fp-353

Hybrid fp-151 and fp-353 fused with the hexa-histidine affinity ligand were produced in E. coli as described previously, respectively (Hwang et al., Biomaterials vol 28, pp 3560-3568, 2007; Gim et al., Biotechnol. Prog. vol 24, pp 1272-1277, 2008)

In brief, E. coli cells were cultured in 7 L LB medium supplemented with 50 μg/mL ampicillin (Sigma) within a 10 L bioreactor (KoBiotech) at 37° C. and 250 rpm. At optical density ($OD_{600}$) of 0.2-0.5, 1 mM (final concentration) isopropyl-β-D-thiogalactopyranoside (IPTG; Sigma) was added to the broth to induce fp-151 expression, and cultured for 8 h at 37° C. and 250 rpm. Following centrifugation of culture broth at 18,000 g for 10 min at 4° C., cell pellets were stored at −80° C. for further analysis. Harvested cell pellets containing hybrid fp-151 were resuspended in 5 mL lysis buffer (10 mM Tris-Cl, 100 mM sodium phosphate, pH 8.0) per gram wet weight. Samples were lysed with constant cell disruption systems (Constant Systems) at 20 kpsi, lysates centrifuged at about 18,000 g for 20 min at 4° C., and the cell debris dissolved in binding buffer (8 M urea, 10 mM Tris-Cl, 100 mM sodium phosphate, pH 8.0) for immobilized metal affinity chromatography (IMAC) purification. IMAC was performed under denaturing conditions using the Acta Prime Purification System (Amersham Biosciences) at room temperature at a rate of 1 mL per min. The affinity purification resin used was 10 mL of Ni-nitrilotriacetate agarose (Qiagen) charged with 10 mL of 0.1 M $NiSO_4$. Target fp-151 was eluted with elution buffer (8 M urea, 10 mM Tris-Cl, 100 mM sodium phosphate, pH 4.5), and dialyzed in 5% (vol/vol) acetic acid buffer overnight at 4° C., using Spectra/Por molecular porous membrane tubing (Spectrum Laboratories). The sample was concentrated by freeze-drying, and finally dissolved in distilled water.

Example 2

Complex Formation Ability of PAGA with DNA

DNA binding activity was determined with electrophoretic DNA retardation. Hybrid MAP (fp-151 or fp-353) (4 mg/mL) was mixed with the plasmid pcDNA/3.1/His/lacZ (133 g/mL; Invitrogen) at ratios (wt/wt) of 0.5:1 to 8:1, and incubated for 30 min at room temperature. Bovine serum albumin (BSA; Sigma) was also mixed with the plasmid at an 8:1 ratio (wt/wt) as a negative control. Samples were separated by electrophoresis at 100 V on 1% (wt/vol) agarose gel containing ethidium bromide, and band retardation was assessed by UV transillumination.

FIG. 1 shows DNA retardation assay to determine the DNA-binding activity of (A) hybrid fp-151 and (B) hybrid fp-353. Lanes: M, DNA size marker; BSA, bovine serum albumin/DNA mixture; NC, DNA only as a negative control; hybrid fp-151, hybrid fp-151/DNA mixture; hybrid fp-353, hybrid fp-353/DNA mixture. Each lane represents the mixed ratio (wt/wt) of protein:DNA. As shown in FIG. 1, a complex of DNA and protein showed reduced charge density and thus existed at upper part of gel.

Example 3

Mammalian Cell Culture and Transfection

Wild-type human 293T (#CRL-11268, ATCC) and mouse NIH/3T3 (#CRL-1658, ATCC) cells were cultured in Dulbecco's modified Eagle's medium (DMEM; Hyclone) supplemented with 10% (vol/vol) fetal bovine serum (FBS; Hyclone) and penicillin/streptavidin (Gibco) at 37° C. in a humidified atmosphere of 5% $CO_2$ and 95% air.

Initially, $2 \times 10^5$ cells were plated onto a 12-well culture plate. At 70-90% confluence, cells were transfected with pcDNA/3.1/His/lacZ that encodes β-galactosidase or pEGFP/C1 (Clontech) encoding enhanced green fluorescence protein (EGFP). A total of 500 ng plasmid was incubated with hybrid MAP (from 1 μg [hybrid MAP:DNA=2:1 (wt/wt)] to 32 μg [hybrid MAP:DNA=64:1 (wt/wt)]) in 100 μL of Opti-MEM™ (Gibco) for 20 min. The DNA: hybrid MAP mixture was added dropwise to cells, and incubated for 48 h in DMEM with 10% FBS & 0~18 mM $CaCl_2$ and without antibiotics.

The transfection efficiency was measured after incubation. Transfected cells were lysed and reporter proteins harvested using the Reporter lysis buffer system (Promega). β-Galactosidase activity was measured using o-nitrophenyl-β-D-galactopyranoside (ONPG; Promega) as a substrate, and absorbance at 420 nm was measured with a UV-vis spectrophotometer (Shimadzu). The fluorescence intensity of EGFP was measured at 488 nm for excitation and 513 nm for emission, using a fluorescence spectrophotometer (Shimadzu). EGFP-expressing fluorescent cells were additionally analyzed by flow cytometer (FACSCalibur; BD Biosciences) and examined by fluorescence microscopy (Olympus). For nuclear staining, transfected cells were fixed with 4% (vol/vol) paraformaldehyde, and permeabilized with 0.1% (vol/vol) Triton X-100. Fixed cells were washed with PBS, and immersed in 0.001% (wt/vol) 4',6-diamidino-2-phenylindole (DAPI) in PBS for 20 min. Finally, cells were fixed with Lisbeth's embedding medium (30 mM Tris-Cl, pH 9.5, 70% glycerol, 50 mg/mL N-propyl gallate), and examined by fluorescence microscopy.

Transfection with 500 ng plasmid DNA only (in the presence and absence of $CaCl_2$) was performed as the negative control. As a positive control, cells were transfected with 500 ng plasmid DNA using 1 μg of Lipofectamine™ 2000 (Invitrogen), which can be added directly to culture medium even in the presence of serum, according to the manufacturer's instructions.

Figure 2:
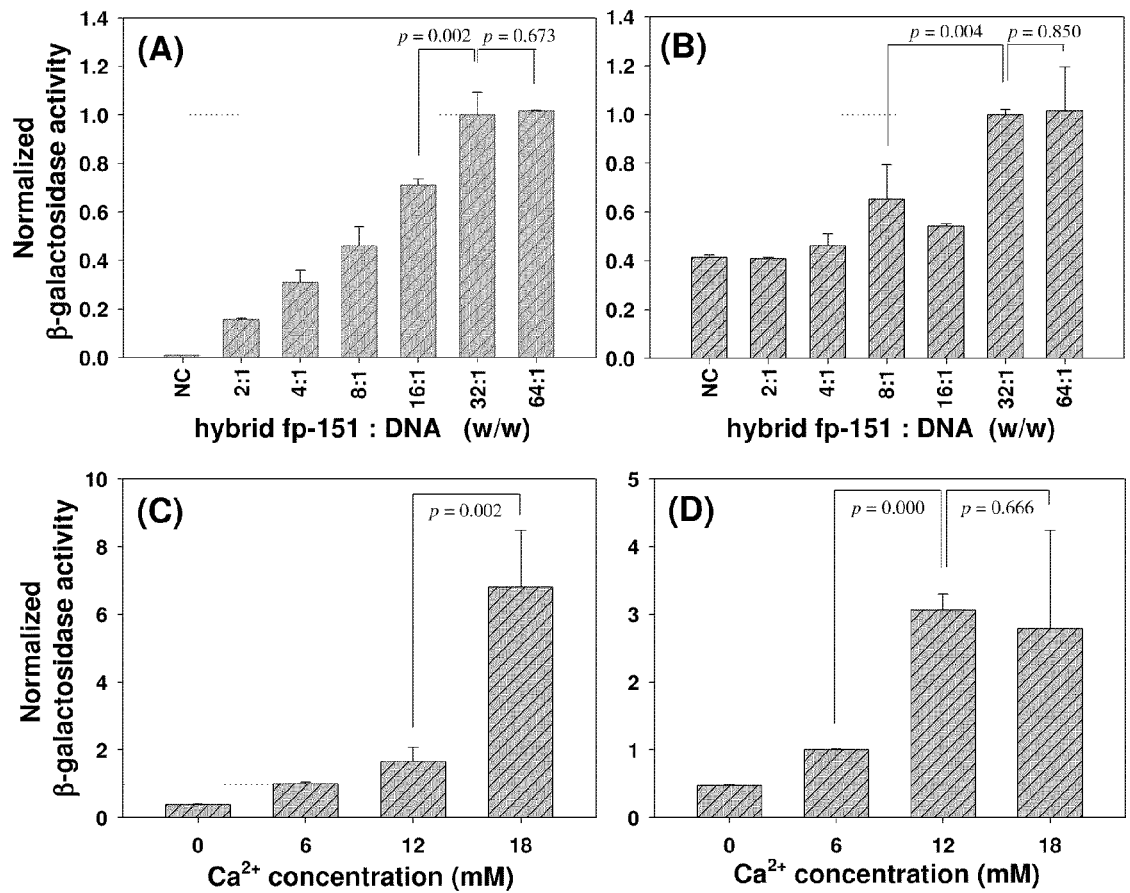
FIG. 2 shows optimization of hybrid fp-151 (A, B) and calcium chloride (C, D) concentrations for efficient transient transfection of lacZ reporter gene into human 293T (A, C) and mouse NIH/3T3 (B, D) cells under serum-presence condition.

FIG. 2 shows optimization of hybrid fp-151 (A, B) and calcium chloride (C, D) concentrations for efficient transient transfection of lacZ reporter gene into human 293T (A, C) and mouse NIH/3T3 (B, D) cells under serum-presence condition. Abbreviations: NC, DNA only as a negative control; 2:1, fp-151:DNA ratio of 2:1 (wt/wt) with 6 mM $CaCl_2$; 4:1, fp-151:DNA ratio of 4:1 (wt/wt) with 6 mM $CaCl_2$; 8:1, fp-151:DNA ratio of 8:1 (wt/wt) with 6 mM $CaCl_2$; 16:1, fp-151:DNA ratio of 16:1 (wt/wt) with 6 mM $CaCl_2$; 32:1, fp-151:DNA ratio of 32:1 (wt/wt) with 6 mM $CaCl_2$; 64:1, fp-151:DNA ratio of 64:1 (wt/wt) with 6 mM $CaCl_2$.

As shown in FIG. 2, the concentrations of the gene-delivering peptide and calcium ion affected the transfection efficiency. As the UV absorbance and fluorescence intensity is higher, the transferection efficiency is high.

Figure 3:
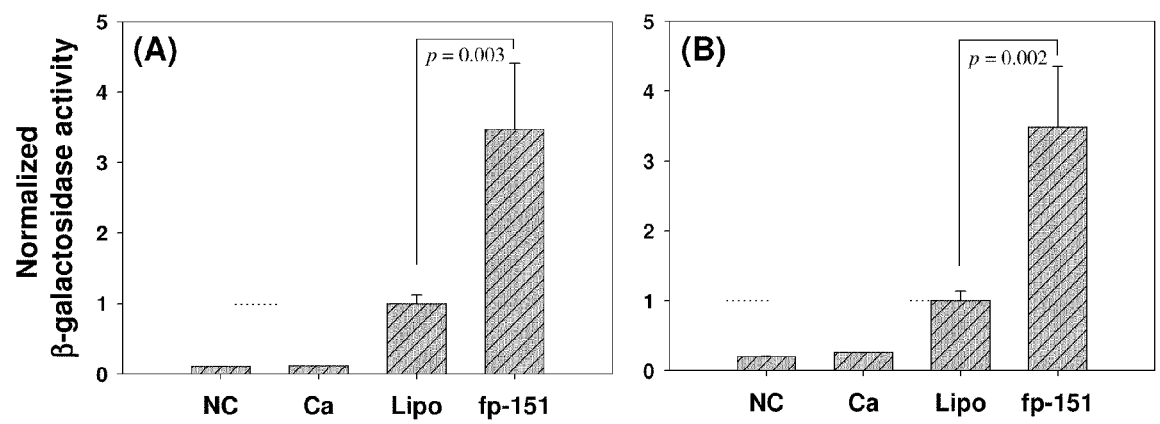
FIG. 3 shows comparison of the transfection efficiencies of lacZ reporter gene into human 293T (A) and mouse NIH/3T3 (B) cells using hybrid fp-151 under serum-presence condition.

FIG. 3 shows comparison of the transfection efficiencies of lacZ reporter gene into human 293T (A) and mouse NIH/3T3 (B) cells using hybrid fp-151 under serum-presence condition. Abbreviations: NC, DNA only as a negative control; Ca, DNA with 18 mM (293T) or 12 mM (NIH/3T3) $CaCl_2$; Lipo, DNA with Lipofectamine™ 2000; fp-151, DNA with hybrid fp-151:DNA ratio of 32:1 (wt/wt) and 18 mM (293T) or 12 mM (NIH/3T) $CaCl_2$. In comparison with control group, the mussel adhesive protein showed high transfection efficiency.

Figure 4:
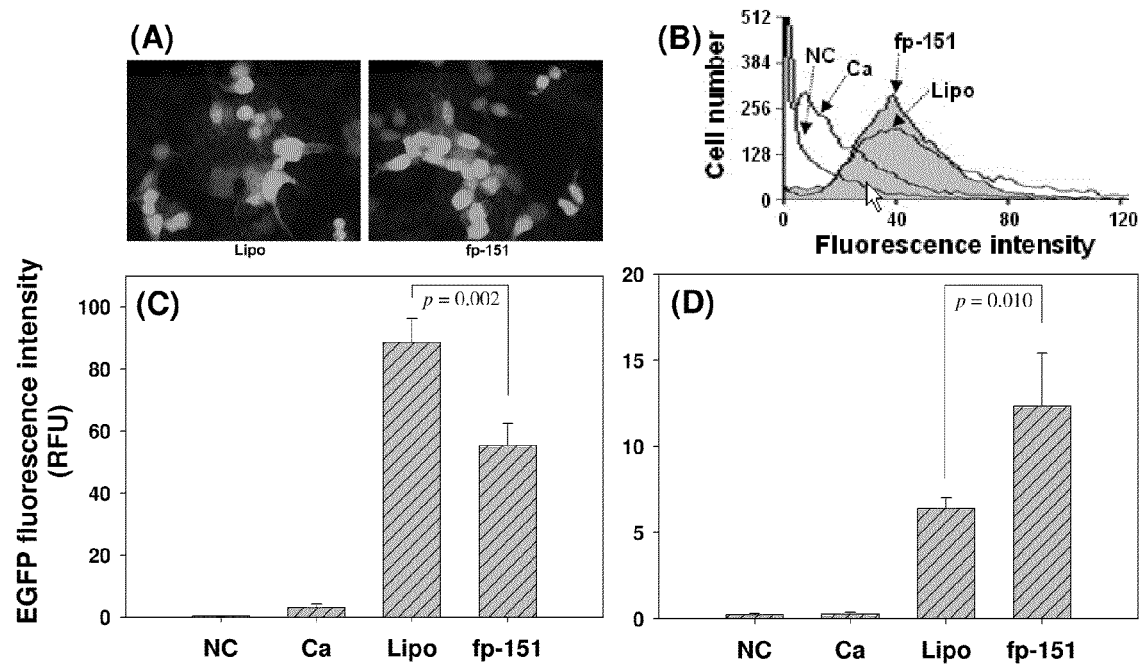
FIG. 4 shows (A) EGFP-expressing fluorescent (green) and DAPI nuclear-stained (blue) cells transfected with Lipofectamine™ 2000 or hybrid fp-151 were observed using fluorescence microscopy (400× magnification) and (B) comparison of the transfection efficiencies of egfp reporter gene into human 293T cells using flow cytometric analyses. Comparison of the expression efficiencies of EGFP reporter in (C) human 293T and (D) mouse NIH/3T3 cells using hybrid fp-151.

FIG. 4 shows (A) EGFP-expressing fluorescent (green) and DAPI nuclear-stained (blue) cells transfected with Lipofectamine™ 2000 or hybrid fp-151 were observed using fluorescence microscopy (400× magnification) and (B) comparison of the transfection efficiencies of egfp reporter gene into human 293T cells using flow cytometric analyses. Comparison of the expression efficiencies of EGFP reporter in (C) human 293T and (D) mouse NIH/3T3 cells using hybrid fp-151. Abbreviations: NC, DNA only as a negative control; Ca, DNA with 18 mM (293T) or 12 mM (NIH/3T3) $CaCl_2$; Lipo, DNA with Lipofectamine™ 2000; fp-151, DNA with hybrid fp-151:DNA ratio of 32:1 (wt/wt) and 18 mM (293T) or 12 mM (NIH/3T) $CaCl_2$.

Figure 5:
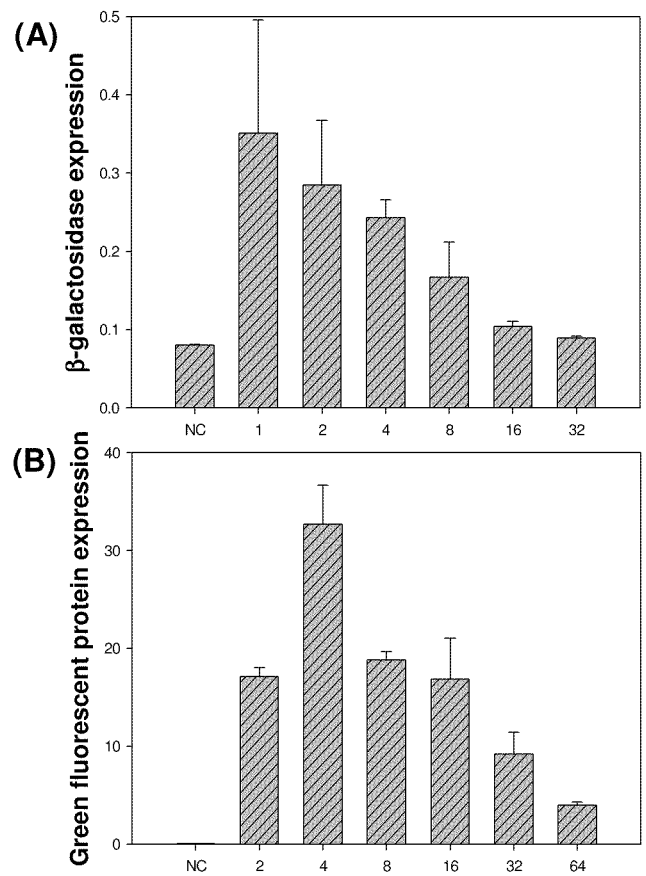
FIG. 5 shows transfection efficiencies of (A) lacZ and (B) GFP reporter gene into human 293T cells using hybrid fp-353 under serum-presence condition.

FIG. 5 shows transfection efficiencies of (A) lacZ and (B) GFP reporter gene into human 293T cells using hybrid fp-353 under serum-presence condition. Abbreviations: NC, DNA only as a negative control; number, relative fp-353 amount (wt) compared to DNA amount (set as 1; wt).

The inventors performed a comparative study with Lipofectamine™ 2000 as a positive control. Lipofectamine™ 2000 is a widely used cationic liposome originally developed for use in even serum-containing medium. Hybrid fp-151/DNA mixtures (32:1 (wt/wt)) were transfected into mammalian cells in the presence of calcium ions (18 mM for 293T and 12 mM for NIH/3T3). Transfection efficiencies using hybrid fp-151 were significantly higher (~3.5-fold) than those with the Lipofectamine-mediated method with lacZ as the reporter gene in both 293T and NIH/3T3 cell lines. To confirm the potency of hybrid fp-151 as the DNA carrier, another reporter gene, egfp, was used for transient transfection. Using hybrid fp-151-mediated transfection, EGFP fluorescence was successfully observed from transfected 293T cells with fluorescence microscopy. In the case of egfp reporter gene transfection into 293T cells, we also performed flow cytometric analyses to compare actual transfection efficiencies. The fp-151-mediated transfection showed comparably similar percentages of EGFP-expressing cells to Lipofectamine™ 2000-based method while negative control and only calcium added cases exhibited minimal transfections. We found that these flow cytometric results had a somewhat correlation with EGFP expression levels from spectrophotometric.

Example 4

Cytotoxic Assays of Transfected Cell Lines 3-(4,5-Dimethylthiazol-2-yl)-2,5-diphenyltetrazolium bromide (MTT) assay (Mossman. 1983) was performed for measuring cytotoxicity after the transient transfection of human 293T and mouse NIH/3T3 cells. Cells ($2 \times 10^5$) were plated in each well of 12-well plates, and transfected with 500 ng of plasmid pcDNA/3.1/His/lacZ using Lipofectamine™ 2000 (1 μg) and hybrid MAP (16 μg) in the presence of 18 mM $CaCl_2$. After 48 h, the culture medium was aspirated, and 500 μL of MTT was added to the wells to allow the formation of formazan crystal for 2 h. Finally, absorbance was measured at 570 nm using a microplate reader (Perkin-Elmer).

Figure 6:
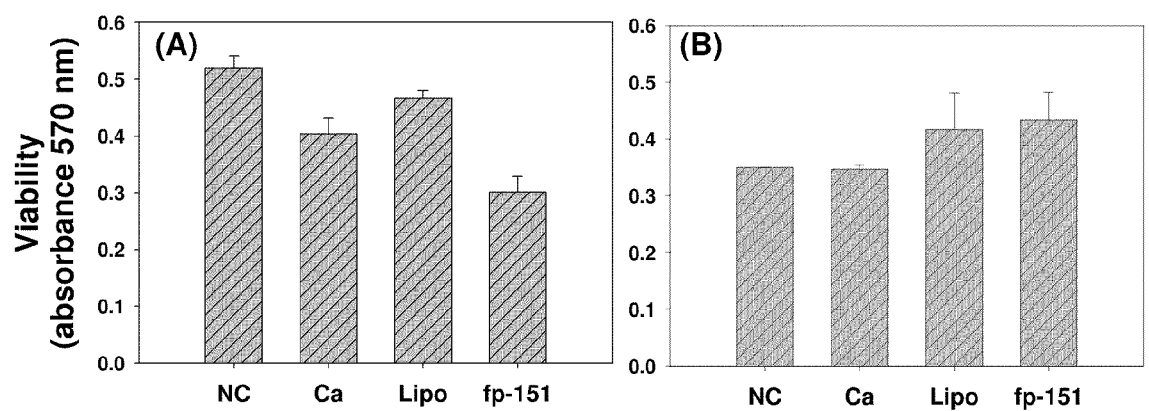
FIG. 6 shows effects of transfection on cell proliferation and viability of human 293T (A) and mouse NIH/3T3 (B) cells using plasmid DNA containing lacZ.

FIG. 6 shows effects of transfection on cell proliferation and viability of human 293T (A) and mouse NIH/3T3 (B) cells using plasmid DNA containing lacZ. Abbreviations: NC, DNA only as a negative control; Ca, DNA with 18 mM (293T) or 12 mM (NIH/3T3) $CaCl_2$; Lipo, DNA with Lipofectamine™ 2000; fp-151, DNA with hybrid fp-151:DNA ratio of 32:1 (wt/wt) and 18 mM (293T) or 12 mM (NIH/3T) $CaCl_2$.

What is claimed is:

1. A method for delivering a nucleic acid-fusion protein complex into a eukaryotic cell, said method comprising
contacting a eukaryotic cell with a complex comprising a nucleic acid and a fusion protein, wherein the fusion protein comprises the formula X-(FP-5)-X, where each X is the same and is chosen from the group consisting of FP-1, FP-2, FP-3, FP-4, FP-6 and SEQ ID NO: 2, and wherein subsequent to the contacting step, the complex enters the eukaryotic cell.

2. The method of claim 1, wherein the gene-delivering peptide further comprises nuclear localization signal peptide or a protein transduction domain.

3. The method of claim 1, wherein the gene-delivering peptide further comprises a purification tag.

4. The method of claim 1, wherein X=FP-1.

5. The method of claim 4, wherein the fusion protein comprises SEQ ID NO:3.

6. The method of claim 1, wherein X=FP-3.

7. The method of claim 6, wherein the fusion protein comprises SEQ ID NO:5.

8. The method of claim 1, wherein the cells are contained in a solution containing a calcium compound.

9. The method of claim 1, wherein the weight ratio of the fusion protein to the nucleic acid is 1:1 to 100:1.

10. The method of claim 1, wherein the nucleic acid is one selected from the group consisting of a genomic DNA, an RNA, an oligonucleotide, and an antisense nucleic acid.

* * * * *

SEQUENCE LISTING

```
<160> NUMBER OF SEQ ID NOS: 17

<210> SEQ ID NO 1
<211> LENGTH: 75
<212> TYPE: PRT
<213> ORGANISM: Artificial Sequence
<220> FEATURE:
```

-continued

<223> OTHER INFORMATION: Mussel Adhesive protein FP-5 derived from
      Mytilus galloprovincialis

<400> SEQUENCE: 1

Ser Ser Glu Glu Tyr Lys Gly Gly Tyr Pro Gly Asn Ser Asn His
1               5                   10                  15

Tyr His Ser Gly Gly Ser Tyr His Gly Ser Gly Tyr His Gly Gly Tyr
                20                  25                  30

Lys Gly Lys Tyr Tyr Gly Lys Ala Lys Lys Tyr Tyr Lys Tyr Lys
        35                  40                  45

Asn Ser Gly Lys Tyr Lys Tyr Leu Lys Lys Ala Arg Lys Tyr His Arg
    50                  55                  60

Lys Gly Tyr Lys Lys Tyr Tyr Gly Gly Ser Ser
65                  70                  75

<210> SEQ ID NO 2
<211> LENGTH: 60
<212> TYPE: PRT
<213> ORGANISM: Artificial Sequence
<220> FEATURE:
<223> OTHER INFORMATION: 6 repeats of FP-1 decapeptides derived from
      Mytilus galloprovincialis

<400> SEQUENCE: 2

Ala Lys Pro Ser Tyr Pro Pro Thr Tyr Lys Ala Lys Pro Ser Tyr Pro
1               5                   10                  15

Pro Thr Tyr Lys Ala Lys Pro Ser Tyr Pro Pro Thr Tyr Lys Ala Lys
                20                  25                  30

Pro Ser Tyr Pro Pro Thr Tyr Lys Ala Lys Pro Ser Tyr Pro Pro Thr
        35                  40                  45

Tyr Lys Ala Lys Pro Ser Tyr Pro Pro Thr Tyr Lys
    50                  55                  60

<210> SEQ ID NO 3
<211> LENGTH: 204
<212> TYPE: PRT
<213> ORGANISM: Artificial Sequence
<220> FEATURE:
<223> OTHER INFORMATION: recombinant mussel adhesive protein FP-151
      derived from Mytilus galloprovincialis

<400> SEQUENCE: 3

Ala Ser Ala Lys Pro Ser Tyr Pro Pro Thr Tyr Lys Ala Lys Pro Ser
1               5                   10                  15

Tyr Pro Pro Thr Tyr Lys Ala Lys Pro Ser Tyr Pro Pro Thr Tyr Lys
                20                  25                  30

Ala Lys Pro Ser Tyr Pro Pro Thr Tyr Lys Ala Lys Pro Ser Tyr Pro
        35                  40                  45

Pro Thr Tyr Lys Ala Lys Pro Ser Tyr Pro Pro Thr Tyr Lys Gly Cys
    50                  55                  60

Ser Ser Glu Glu Tyr Lys Gly Gly Tyr Tyr Pro Gly Asn Ser Asn His
65                  70                  75                  80

Tyr His Ser Gly Gly Ser Tyr His Gly Ser Gly Tyr His Gly Gly Tyr
                85                  90                  95

Lys Gly Lys Tyr Tyr Gly Lys Ala Lys Lys Tyr Tyr Lys Tyr Lys
        100                 105                 110

Asn Ser Gly Lys Tyr Lys Tyr Leu Lys Lys Ala Arg Lys Tyr His Arg
    115                 120                 125

Lys Gly Tyr Lys Lys Tyr Tyr Gly Gly Ser Ser Glu Phe Glu Phe Ala
        130                 135                 140

```
Lys Pro Ser Tyr Pro Pro Thr Tyr Lys Ala Lys Pro Ser Tyr Pro Pro
145                 150                 155                 160

Thr Tyr Lys Ala Lys Pro Ser Tyr Pro Pro Thr Tyr Lys Ala Lys Pro
            165                 170                 175

Ser Tyr Pro Pro Thr Tyr Lys Ala Lys Pro Ser Tyr Pro Pro Thr Tyr
        180                 185                 190

Lys Ala Lys Pro Ser Tyr Pro Pro Thr Tyr Lys Leu
    195                 200

<210> SEQ ID NO 4
<211> LENGTH: 46
<212> TYPE: PRT
<213> ORGANISM: Artificial Sequence
<220> FEATURE:
<223> OTHER INFORMATION: Mussel adhesive protein FP-3A derived from
      Mytilus galloprovincialis

<400> SEQUENCE: 4

Ala Asp Tyr Tyr Gly Pro Lys Tyr Gly Pro Pro Arg Arg Tyr Gly Gly
1               5                   10                  15

Gly Asn Tyr Asn Arg Tyr Gly Arg Arg Tyr Gly Gly Tyr Lys Gly Trp
            20                  25                  30

Asn Asn Gly Trp Lys Arg Gly Arg Trp Gly Arg Lys Tyr Tyr
        35                  40                  45

<210> SEQ ID NO 5
<211> LENGTH: 173
<212> TYPE: PRT
<213> ORGANISM: Artificial Sequence
<220> FEATURE:
<223> OTHER INFORMATION: recombinant mussel adhesive protein FP-353
      derived from Mytilus galloprovincialis

<400> SEQUENCE: 5

Ala Asp Tyr Tyr Gly Pro Lys Tyr Gly Pro Pro Arg Arg Tyr Gly Gly
1               5                   10                  15

Gly Asn Tyr Asn Arg Tyr Gly Arg Arg Tyr Gly Gly Tyr Lys Gly Trp
            20                  25                  30

Asn Asn Gly Trp Lys Arg Gly Arg Trp Gly Arg Lys Tyr Tyr Glu Phe
        35                  40                  45

Ser Ser Glu Glu Tyr Lys Gly Gly Tyr Tyr Pro Gly Asn Ser Asn His
    50                  55                  60

Tyr His Ser Gly Gly Ser Tyr His Gly Ser Gly Tyr His Gly Gly Tyr
65                  70                  75                  80

Lys Gly Lys Tyr Gly Lys Ala Lys Lys Tyr Tyr Tyr Lys Tyr Lys
                85                  90                  95

Asn Ser Gly Lys Tyr Lys Tyr Leu Lys Lys Ala Arg Lys Tyr His Arg
            100                 105                 110

Lys Gly Tyr Lys Lys Tyr Lys Tyr Gly Gly Ser Ser Lys Leu Ala Asp Tyr
        115                 120                 125

Tyr Gly Pro Lys Tyr Gly Pro Pro Arg Arg Tyr Gly Gly Gly Asn Tyr
    130                 135                 140

Asn Arg Tyr Gly Arg Arg Tyr Gly Gly Tyr Lys Gly Trp Asn Asn Gly
145                 150                 155                 160

Trp Lys Arg Gly Arg Trp Gly Arg Lys Tyr Tyr Leu Glu
                165                 170

<210> SEQ ID NO 6
<211> LENGTH: 12
```

```
<212> TYPE: PRT
<213> ORGANISM: Artificial Sequence
<220> FEATURE:
<223> OTHER INFORMATION: Nuclear Localization signal peptide example 1
      derived from simian virus 40

<400> SEQUENCE: 6

Pro Lys Lys Lys Arg Lys Val Glu Asp Pro Tyr Cys
  1               5                  10

<210> SEQ ID NO 7
<211> LENGTH: 11
<212> TYPE: PRT
<213> ORGANISM: Artificial Sequence
<220> FEATURE:
<223> OTHER INFORMATION: Nuclear Localization signal peptide example 2
      derived from simian virus 40

<400> SEQUENCE: 7

Cys Gly Gly Pro Lys Lys Lys Arg Lys Val Gly
  1               5                  10

<210> SEQ ID NO 8
<211> LENGTH: 8
<212> TYPE: PRT
<213> ORGANISM: Artificial Sequence
<220> FEATURE:
<223> OTHER INFORMATION: Nuclear localization signal peptide example 3
      derived from simian virus 40

<400> SEQUENCE: 8

Pro Pro Lys Lys Lys Arg Lys Val
  1               5

<210> SEQ ID NO 9
<211> LENGTH: 10
<212> TYPE: PRT
<213> ORGANISM: Artificial Sequence
<220> FEATURE:
<223> OTHER INFORMATION: Protein transduction domain example 1 derived
      from human immunodeficiency virus-1

<400> SEQUENCE: 9

Arg Lys Lys Lys Arg Arg Gln Arg Arg Arg
  1               5                  10

<210> SEQ ID NO 10
<211> LENGTH: 34
<212> TYPE: PRT
<213> ORGANISM: Artificial Sequence
<220> FEATURE:
<223> OTHER INFORMATION: Protein tranduction domain example 2 derived
      from herpes simplex virus type 1

<400> SEQUENCE: 10

Asp Ala Ala Thr Ala Thr Arg Gly Arg Ser Ala Ala Ser Arg Pro Thr
  1               5                  10                  15

Glu Arg Pro Arg Ala Pro Ala Arg Ser Ala Ser Arg Pro Arg Arg Pro
                 20                  25                  30

Val Glu

<210> SEQ ID NO 11
<211> LENGTH: 16
<212> TYPE: PRT
<213> ORGANISM: Artificial Sequence
<220> FEATURE:
<223> OTHER INFORMATION: Protein transduction domain example 2 derived
      from Drosophila melanogaster
```

<400> SEQUENCE: 11

Arg Gln Ile Lys Ile Trp Phe Gln Asn Arg Arg Met Lys Trp Lys Lys
1               5                   10                  15

<210> SEQ ID NO 12
<211> LENGTH: 21
<212> TYPE: PRT
<213> ORGANISM: Artificial Sequence
<220> FEATURE:
<223> OTHER INFORMATION: Protein transduction domain example 4

<400> SEQUENCE: 12

Ala Gly Tyr Leu Leu Gly Lys Ile Asn Leu Lys Ala Leu Ala Ala Leu
1               5                   10                  15

Ala Lys Lys Ile Leu
            20

<210> SEQ ID NO 13
<211> LENGTH: 6
<212> TYPE: PRT
<213> ORGANISM: Artificial Sequence
<220> FEATURE:
<223> OTHER INFORMATION: Purification tag: (His)6

<400> SEQUENCE: 13

His His His His His His
1               5

<210> SEQ ID NO 14
<211> LENGTH: 8
<212> TYPE: PRT
<213> ORGANISM: Artificial Sequence
<220> FEATURE:
<223> OTHER INFORMATION: Purification tag: FLAG tag

<400> SEQUENCE: 14

Asp Tyr Lys Asp Asp Asp Asp Lys
1               5

<210> SEQ ID NO 15
<211> LENGTH: 6
<212> TYPE: PRT
<213> ORGANISM: Artificial Sequence
<220> FEATURE:
<223> OTHER INFORMATION: HA (an epitope derived from the Influenza
      protein haemagglutinin) tag

<400> SEQUENCE: 15

Tyr Pro Tyr Asp Val Pro
1               5

<210> SEQ ID NO 16
<211> LENGTH: 10
<212> TYPE: PRT
<213> ORGANISM: Artificial Sequence
<220> FEATURE:
<223> OTHER INFORMATION: MYC (an epitope derived from the human proto-
      oncoprotein) tag-1

<400> SEQUENCE: 16

Ile Leu Lys Lys Ala Thr Ala Tyr Ile Leu
1               5                   10

<210> SEQ ID NO 17
<211> LENGTH: 10
<212> TYPE: PRT

```
<213> ORGANISM: Artificial Sequence
<220> FEATURE:
<223> OTHER INFORMATION: MYC (an epitope derived from the human proto-
      oncoprotein) tag-2

<400> SEQUENCE: 17

Glu Gln Lys Leu Ile Ser Glu Glu Asp Leu
 1               5                  10
```